(12) United States Patent
Takami et al.

(10) Patent No.: US 6,328,690 B1
(45) Date of Patent: Dec. 11, 2001

(54) AIR FEEDING DEVICE FOR ENDOSCOPE

(75) Inventors: Satoshi Takami; Kazuhiro Yamazaki; Noriaki Takahashi, all of Saitama-ken (JP)

(73) Assignee: Asahi Kogaku Kogyo Kabushiki Kaisha, Tokyo (JP)

(*) Notice: Subject to any disclaimer, the term of this patent is extended or adjusted under 35 U.S.C. 154(b) by 0 days.

(21) Appl. No.: 09/345,004

(22) Filed: Jul. 2, 1999

(30) Foreign Application Priority Data

Jul. 3, 1998 (JP) .................................................. 10-188868
Sep. 3, 1998 (JP) .................................................. 10-250145
Sep. 11, 1998 (JP) .................................................. 10-258474

(51) Int. Cl.$^7$ ................................ A61B 1/12; F04B 49/06
(52) U.S. Cl. ..................... 600/159; 600/158; 417/44.2; 417/28
(58) Field of Search .......................... 417/44.2, 26, 28; 600/158, 159, 118; 137/624.11

(56) References Cited

U.S. PATENT DOCUMENTS

| | | | |
|---|---|---|---|
| 4,201,517 | * 5/1980 | Ferguson | 417/26 X |
| 4,863,355 | * 9/1989 | Odagiri et al. | 417/28 X |
| 4,969,801 | * 11/1990 | Haseley et al. | 417/28 X |
| 6,095,971 | * 8/2000 | Takashi | 600/159 |
| 6,132,369 | * 12/2000 | Takashi | 600/159 |
| 6,193,649 | * 2/2001 | Takami et al. | 600/158 |

* cited by examiner

*Primary Examiner*—Charles G. Freay
*Assistant Examiner*—David J. Torrente
(74) *Attorney, Agent, or Firm*—Greenblum & Bernstein, P.L.C.

(57) ABSTRACT

An air feeding device for endoscope system includes an air compressor that compresses air and feeds the air in a sealed space, and a pressure sensor that detects air pressure in the sealed space. Further, a pressure setting device and a pressure controller are provided. The pressure setting device is used for setting a pressure value to be achieved in the sealed space, and the pressure controller turns ON and OFF the compressor in accordance with the air pressure detected by the pressure sensor and the pressure value set by the pressure setting device. The air feeding device has a main valve. An inlet of the main valve is connected to the sealed space, and an outlet of the main valve is connected to an outlet of the air feeding device. By opening the main valve, the air enclosed in the sealed space is discharged from the outlet to strike an object at a certain pressure.

21 Claims, 14 Drawing Sheets

AIR FEEDING DEVICE FOR ENDOSCOPE

BACKGROUND OF THE INVENTION

The present invention relates to an air feeding device for an endoscope to feed air into body cavity.

Conventionally, an air feeding device for an endoscope has been known. The air feeding device has an air compressor which compresses the air, and by opening/closing a valve, the air is fed to the human cavity through a tube such as a forceps channel of an endoscope. In such an air feeding device, in order to control the pressure of the air fed therefrom, a pressure control valve is provided. The pressure control valve varies the cross sectional area of a path where the air flows to vary the pressure of the discharged air.

In the air feeding device, the pressure control valve only lowers the pressure of the discharged air. Therefore, in order to control the pressure over a relatively wide range, a large compressor, which is capable of feeding the air at a relatively high pressure, should be provided. Generally, such a compressor should be driven all the time, which generates continuous noise when the endoscope is used for operation. Further, in such a conventional air feeding device, due to a structure of the pressure control valve, it is impossible to feed the air so as to strike an object at a very small pressure, and thus, it is impossible to control the air pressure accurately within a wide range between a very low pressure and a very high pressure.

There has been known a method for detecting hardness of a foreign body in the human cavity by applying air. There has also been known a method for diagnosing organs inside the human cavity by applying air intermittently. In order to use the air feeding device for such diagnosing system, the air feeding device is required to be able to generate a stable and continuous air flow or intermittent air flow, at a relatively low pressure.

SUMMARY OF THE INVENTION

It is therefore an object of the present invention to provide an improved air feeding device which is capable of generating a stable and continuous air flow or intermittent air flow, at a relatively low pressure.

For the above object, according to the present invention, there is provided an air feeding device for an endoscope system, which is provided with: an air compressor that compresses air and feeds the air into a sealed space; a pressure sensor that detects air pressure in the sealed space; a pressure setting device through which a pressure value in the sealed space to be adjusted is set; a pressure controller that turns the compressor ON and OFF in accordance with the air pressure detected by the pressure sensor and the pressure value set by the pressure setting device; and a main valve, an inlet of the main valve being connected to the sealed space, an outlet of the main valve being connected to an outlet of the air feeding device.

Since the air is once compressed in the sealed space, the feeding system does not require a large compressor. Further, the feeding device is capable of adjusting the pressure of the air discharged from the outlet.

Optionally, the pressure controller may include a comparator which compares output of the pressure sensor with a reference value which is determined based on the pressure value set by the pressure setting device, and wherein the pressure controller turns ON or OFF the compressor depending on the comparison result of the comparator.

With this configuration, since the compressor is not continuously operating, the noise can be reduced.

In a particular case, the pressure controller defines first and second reference values based on the pressure value set by the pressure setting device. The first reference value is greater than the pressure value, and the second reference value is less than the pressure value.

Further, the pressure controller includes a comparator, and turns OFF the compressor if the pressure detected by the pressure sensor is increasing and the pressure detected by the pressure sensor reaches the first reference value. Further, the pressure controller turns ON the compressor if the pressure is decreasing and the pressure reaches the second reference value.

With this configuration, a so-called hysteresis characteristic can be achieved, and thus, a hunting phenomenon in turning ON and OFF the compressor can be avoided.

According to another aspect of the invention, there is provided an air feeding device for endoscope system which is provided with: an air compressor that compresses air and feeds the air in a sealed space; an air tank forming part of the sealed space; a pressure sensor that detects air pressure in the sealed space; a pressure setting device through which a pressure value in the sealed space to be adjusted is set; a pressure controlling valve that releases air in the sealed space; a pressure controller that turns ON or OFF the compressor and/or turns ON or OFF the pressure controlling valve in accordance with the air pressure detected by the pressure sensor and the pressure value set by the pressure setting device; an air feeding valve, an inlet of the air feeding valve being connected to the sealed space, an outlet of the air feeding valve being connected to an outlet of the air feeding device.

Optionally, the sealed space may be defined as a space between the compressor and the air feeding valve, the air tank being arranged between the compressor and the air feeding valve, wherein the air feeding device is further provided with tube members for connecting the compressor and the air tank, and for connecting the air tank and the air feeding valve.

Preferably, a volume of the air tank is greater than a volume of the sealed space excluding the volume of the air tank.

Optionally, the air feeding device may be provided with an air filter which is inserted within the sealed space.

In particular case, the pressure controller defines first and second reference values based on the pressure value set by the pressure setting device, the first reference value being greater than the pressure value, the second reference value being less than the pressure value. The pressure controller turns OFF the compressor if the pressure detected by the pressure sensor is greater than the first reference value, and turns ON the compressor if the pressure detected by the pressure sensor is less than the second reference value.

Optionally or alternatively, the pressure controller may control the pressure control valve to open if the pressure detected by the pressure sensor is greater than the first reference value, and may control the pressure control valve to close if the pressure detected by the pressure sensor is less than the second reference value.

According to a further aspect of the invention, there is provided an air feeding device for endoscope system which is provided with an air compressor that compresses air and feed the air in a sealed space; a pressure sensor that detects air pressure in the sealed space; a pressure controller that turns ON and OFF the compressor in accordance with the air pressure detected by the pressure sensor and a predetermined pressure value; and a main valve, an inlet of the main valve being connected to the sealed space, an outlet of the main valve being connected to an outlet of the air feeding device. The air feeding device is further provided with a pressure setting device through which a pressure value in the sealed space to be adjusted is set; and an enter switch that is manually operated to make the pressure value set by the setting device effective. In this case, when the pressure value is set by the pressure setting device and the enter switch is operated, the pressure controller controls the compressor in accordance with the air pressure detected by the pressure sensor and the pressure value set by the pressure setting device.

With this configuration, until the enter switch is operated, the newly set or currently set pressure value will not be made effective, and therefore unnecessary change of the pressure can be avoided. Further, the pressure can be adjusted upon operation of the enter switch, the pressure control operation can be performed effectively.

According to a further aspect of the invention, there is provided an air feeding device for endoscope system which is provided with: an air compressor that compresses air and feeds the air in a sealed space; an air tank forming part of the sealed space; a pressure sensor that detects air pressure in the sealed space; a pressure controlling valve that releases air in the sealed space; a pressure controller that turns ON or OFF the compressor and/or turns ON or OFF the pressure controlling valve in accordance with the air pressure detected by the pressure sensor and a predetermined pressure value; an air feeding valve, an inlet of the air feeding valve being connected to the sealed space, an outlet of the air feeding valve being connected to an outlet of the air feeding device; a pressure setting device through which a pressure value in the sealed space to be adjusted is set; and an enter switch that is manually operated to make the pressure value set by the setting device effective. Also in this case, when the pressure value is set by the pressure setting device and the enter switch is operated, the pressure controller controls the compressor and the pressure controlling valve in accordance with the air pressure detected by the pressure sensor and the pressure value set by the pressure setting device.

Optionally, the sealed space may be defined as a space between the compressor and the air feeding valve, the air tank being arranged between the compressor and the air feeding valve, and the air feeding device further provided with tube members for connecting the compressor and the air tank, and for connecting the air tank and the air feeding valve.

In order to obtain a stable output, it is preferable that a volume of the air tank is greater than a volume of the sealed space excluding the volume of the air tank.

Optionally, the pressure controller defines first and second reference values based on the pressure value set by the pressure setting device, the first reference value being greater than the pressure value, the second reference value being less than the pressure value, and the pressure controller turns OFF the compressor if the pressure detected by the pressure sensor is greater than the first reference value. Further, the pressure controller turns ON the compressor if the pressure detected by the pressure sensor is less than the second reference value.

Further optionally, the pressure controller defines first and second reference values based on the pressure value set by the pressure setting device, the first reference value being greater than the pressure value, the second reference value being less than the pressure value. The pressure controller controls the pressure control valve to open if the pressure detected by the pressure sensor is greater than the first reference value, and controls the pressure control valve to close if the pressure detected by the pressure sensor is less than the second reference value.

DESCRIPTION OF THE ACCOMPANYING DRAWINGS

FIG. 1 schematically shows an entire air feeding system according to a first embodiment of the invention;

FIG. 2 schematically shows a structure of the air feeding device and a control system thereof;

FIGS. 3A through 3D show a graph illustrating a relationship between the changes of the pressure in the air tube, turning ON and OFF of the compressor, open and close status of the main valve, and the air discharging status;

FIG. 4 schematically shows an entire air feeding system according to a second embodiment of the invention;

FIG. 5 is a rear view of the air feeding device shown in FIG. 4;

FIG. 6 schematically shows an arrangement of main elements inside the air feeding device shown in FIG. 4 when viewed from the top;

Figure 12:
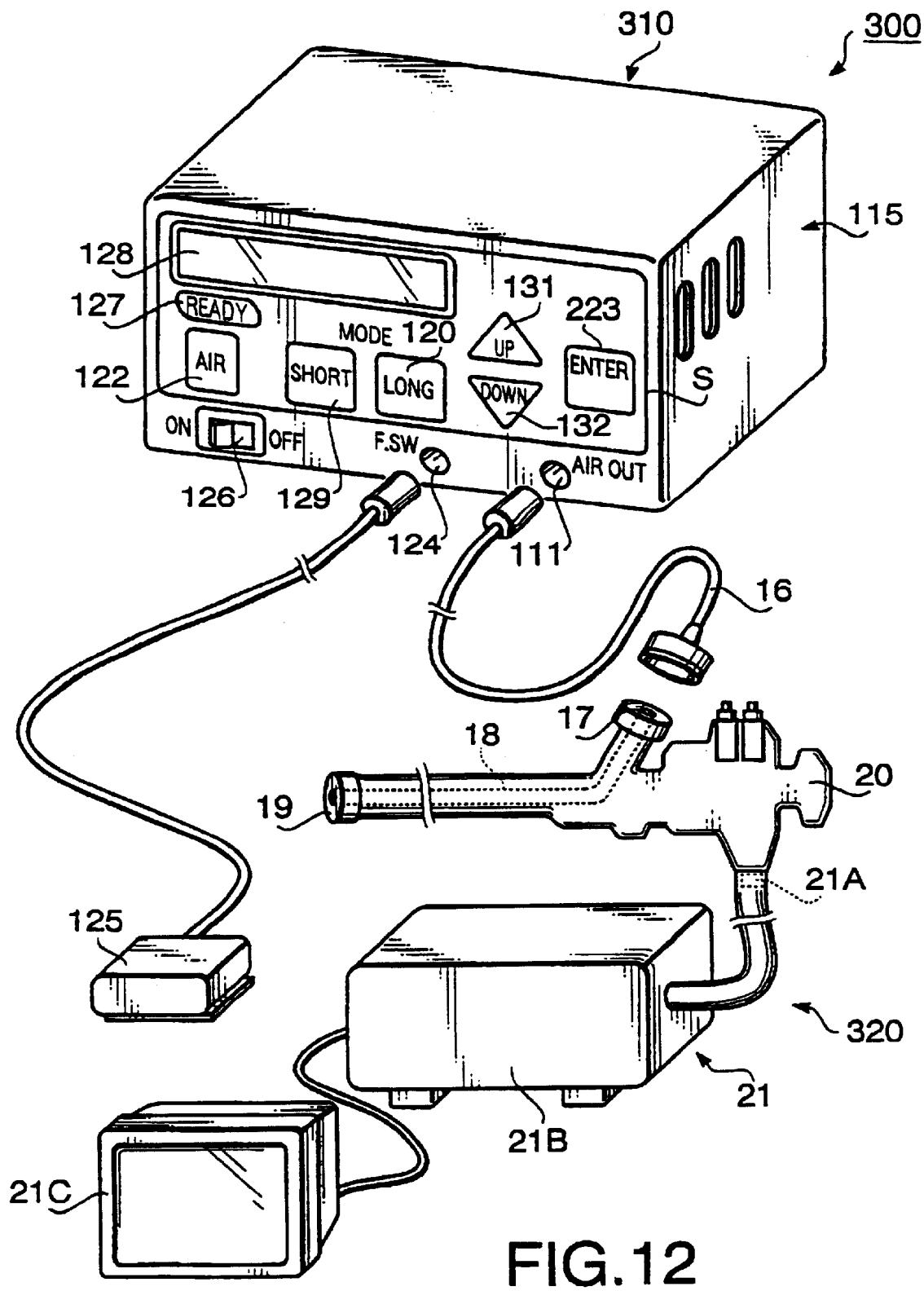
Figure 13:
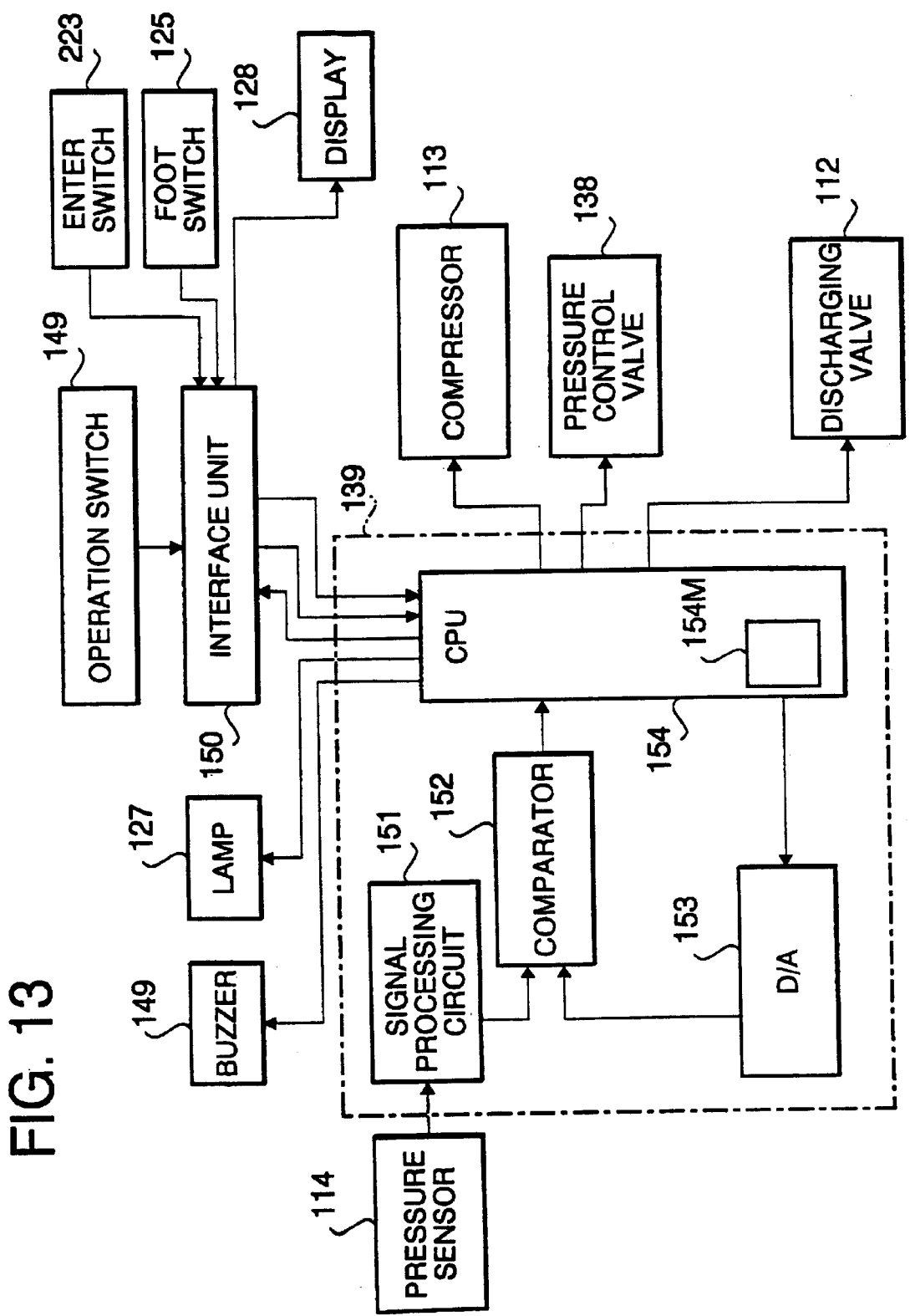
Figure 14:
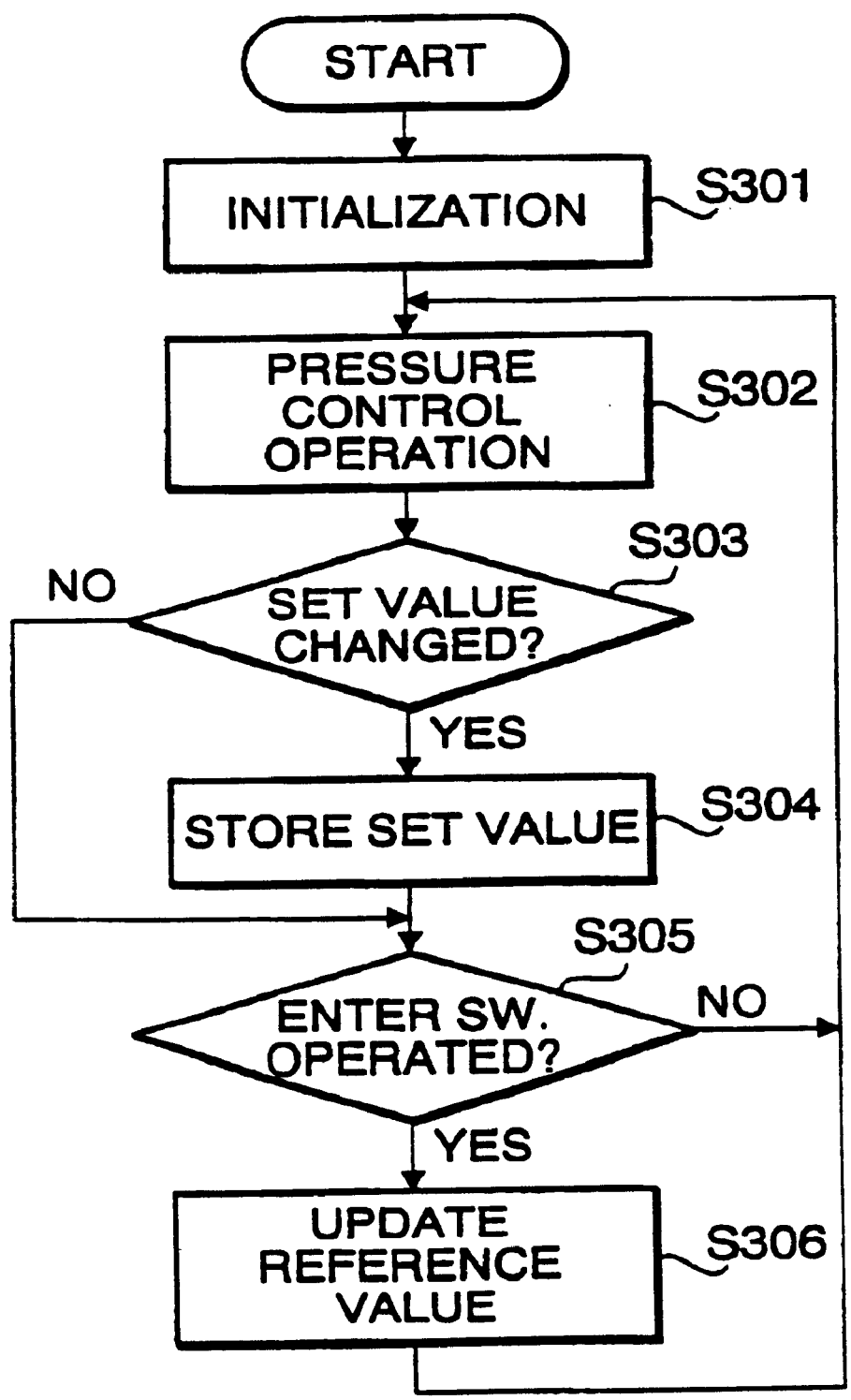

FIG. 12 schematically shows an entire air feeding system according to a third embodiment of the invention;

FIG. 13 is a block diagram showing the control system of the air feeding device; and FIG. 14 is a flowchart illustrating the reference data setting procedure.

DESCRIPTION OF THE EMBODIMENTS

Hereinafter, the invention will be described with reference to the accompanying drawings.

[First Embodiment]

Figure 1:
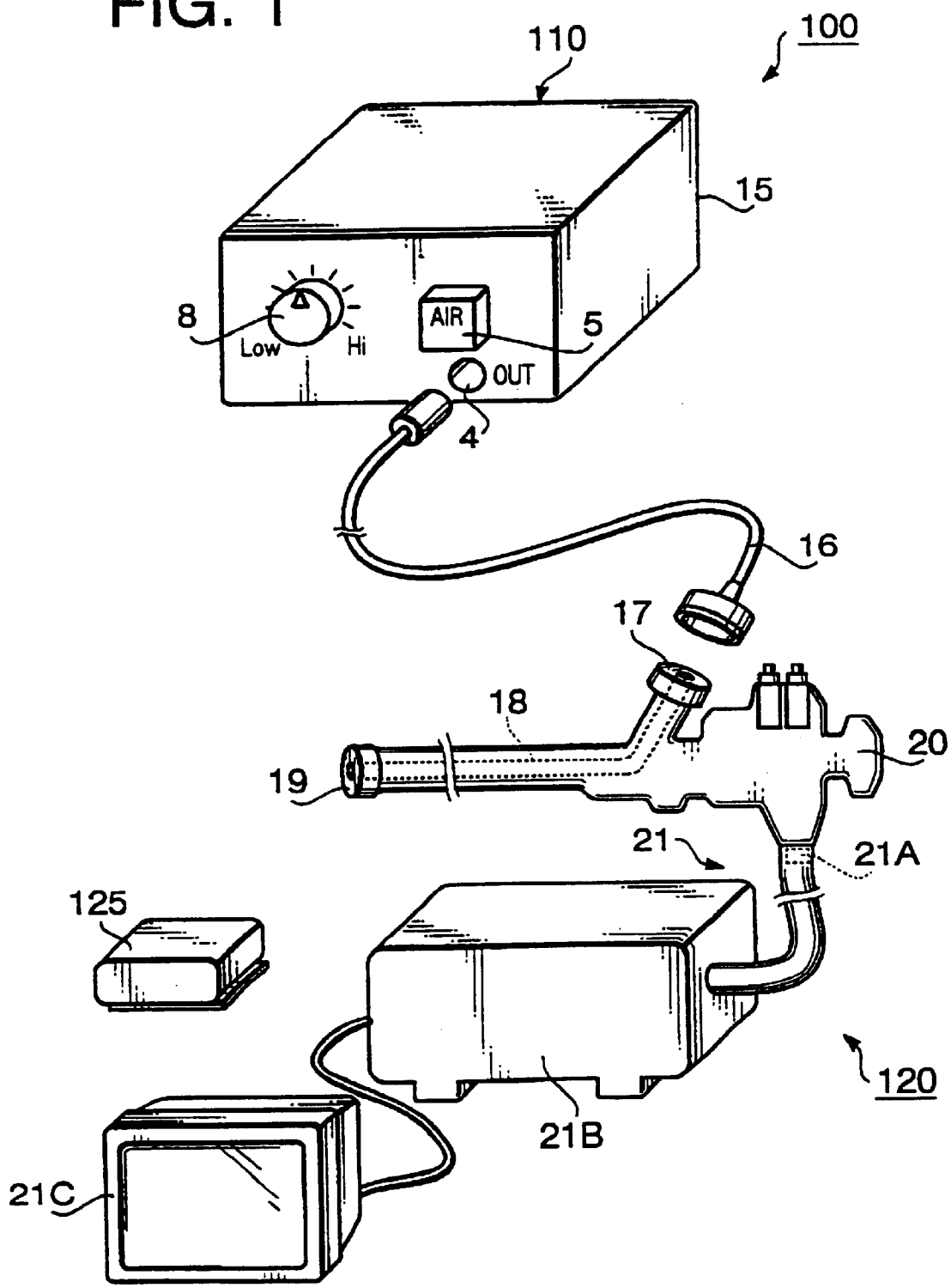

FIG. 1 schematically shows an entire air feeding system 100 according to a first embodiment of the invention.

The endoscope system 100 is provided with an air feeding device 110, and an endoscope system 120.

The air feeding device 110 has a casing 15, on which a pressure setting dial 8, an air feeding button 5, and an air discharging port 4 are provided. A desired air pressure is set by turning the pressure setting dial 8 within a predetermined pressure range. By depressing the air feeding button, the air is discharged from the outlet 4 at the pressure set with use of the pressure setting dial 8.

The endoscope system 120 includes an endoscope 20 and an image processor 21. The endoscope 20 is formed with a forceps channel 18. In this system, the air discharged from the air feeding device 110 is introduced in and flows through the forceps channel 18. In order to introduce the air from the air feeding device 110 to the forceps channel 18, a connection tube 16 is used. An end of the connection tube 16 is connected to the air outlet 4 of the air feeding device 110, and the other end of the connection tube 16 is connected to the inlet 17 of the forceps channel 18. Thus, the air discharged from the air feeding device 110 flows in the connection tube 16 and the forceps channel 18, and discharged out of an outlet 19 of the forceps channel 18.

The image processor 21 includes an imaging device 21A for capturing an optical image formed by the endoscope 20 and output an image signal, an signal processing device 21B for processing the image signal, and a display 21C for display an image in accordance with the image signal output from the image processing device 21B.

In the air feeding system shown in FIG. 1, the air is discharged from the air feeding device 110 only while the air feeding button 5 is being depressed.

Figure 2:
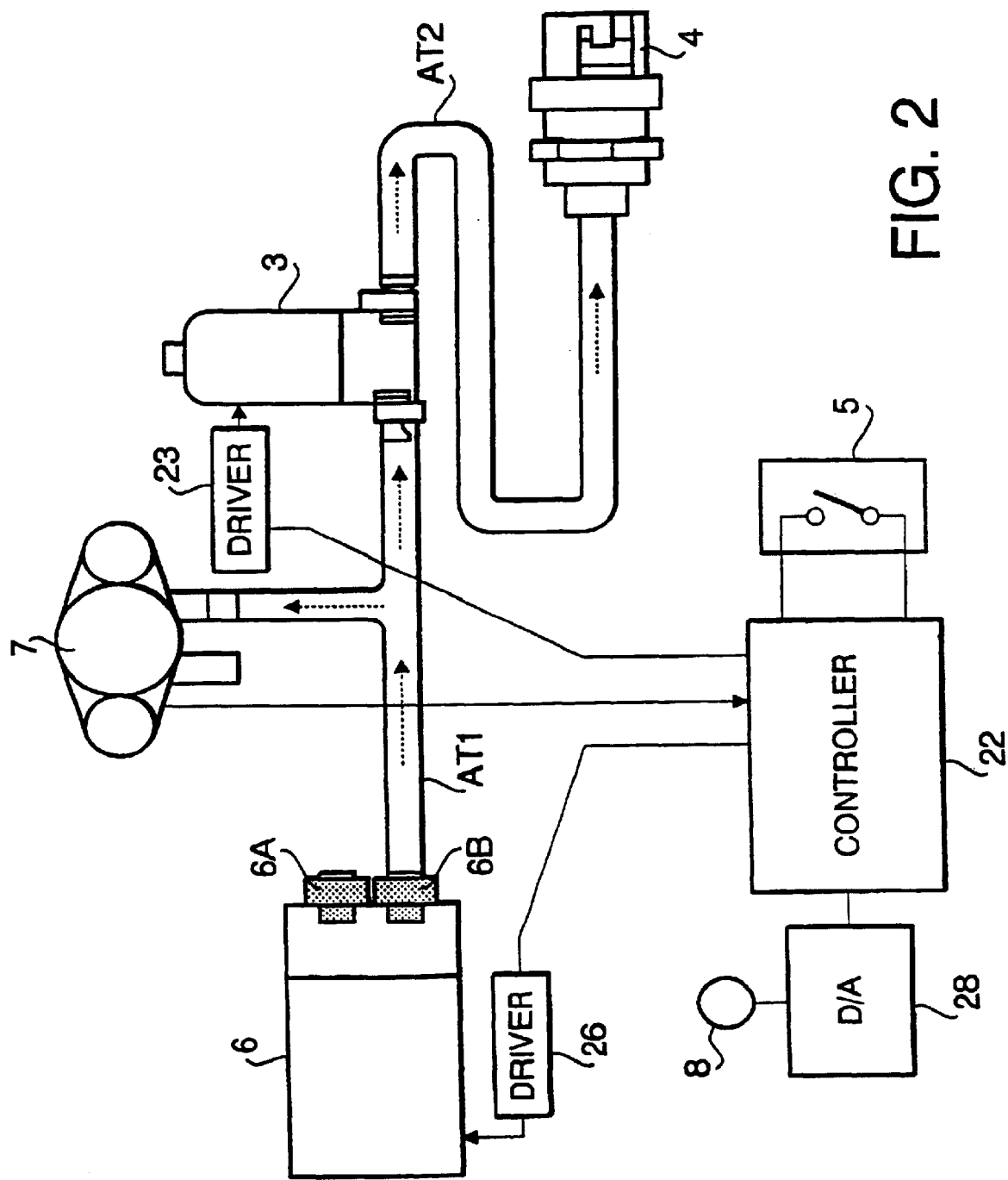
Figure 3:
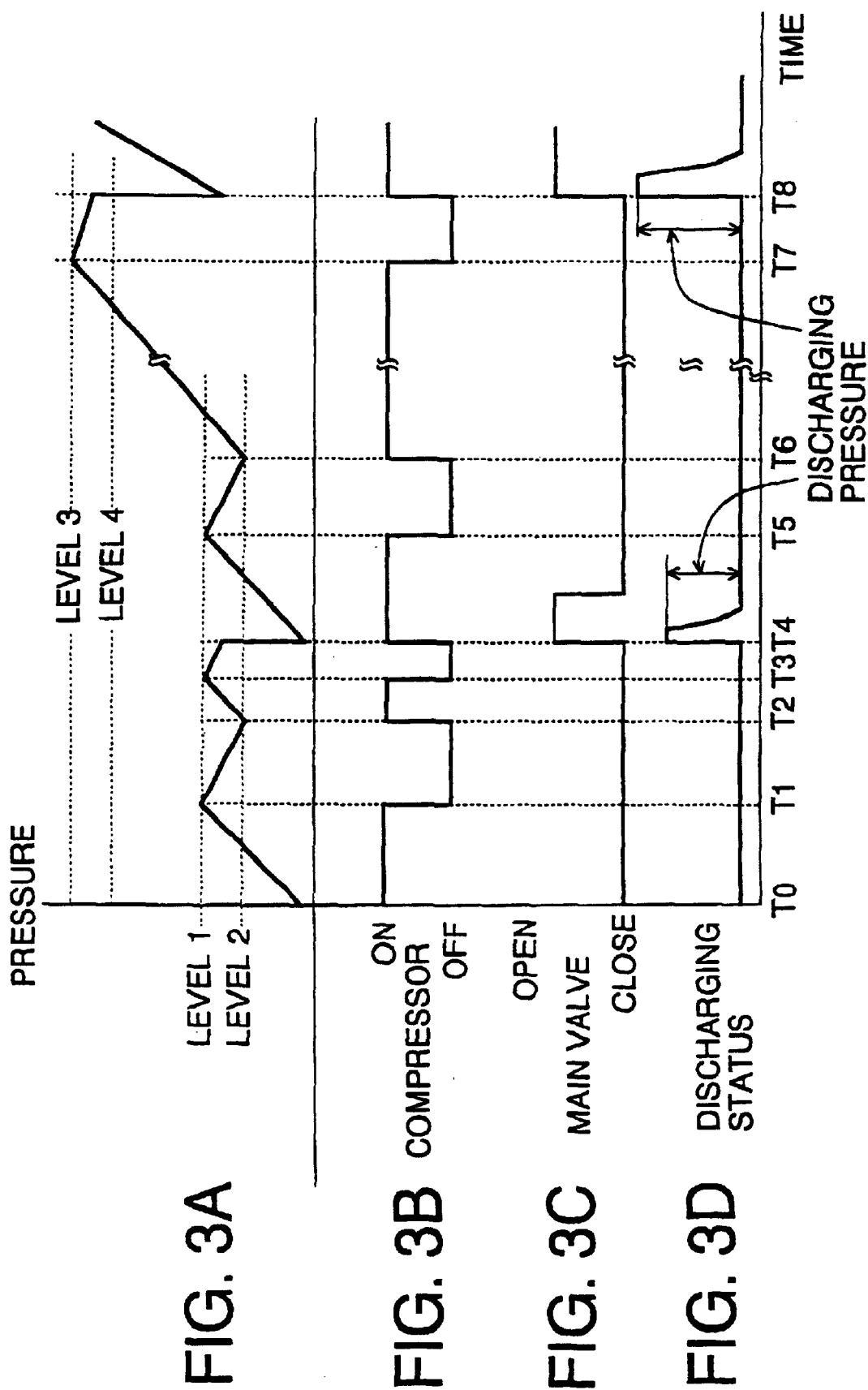

FIG. 2 schematically shows a structure of the air feeding device 110 and a control system thereof.

As shown in FIG. 2, the air feeding device 110 is provided with a compressor 6 which draws in the air from an intake 6A and discharges the air from the outlet 6B to an air tube AT1. The air tube AT1 diverges into two tubes, one of which is connected to an intake of a main valve 3 and the other is connected to a pressure sensor 7. The intake 6A and the outlet 6B respectively have backflow valves. The pressure sensor 7 detects the pressure of the enclosed air (i.e., the air enclosed in the sealed space: AT1). Further, the main valve 3 is usually in a closed state. Thus, the portion of the air feeding device 110 connected with the compressor 6, the sensor 7, and the main valve 3 constitute a sealed space.

It should be noted that, in this embodiment, the pressure sensor 7 outputs a DC voltage in accordance with the pressure of the air in the air tube AT1. Specifically, the pressure sensor 7 outputs a higher voltage when the pressure is higher.

An outlet of the main valve 3 is connected with an end of an air tube AT2, the other end of which is connected to the outlet 4. In FIG. 2, directions in which the air flows are indicated by arrows.

The air feeding device 110 is further provided with a controller 22. The controller 22 is connected with a set pressure detecting circuit 28 which detects the value set by an operator with use of the pressure setting dial 8. The controller 22 is also connected with the air feeding button 5 and detects ON/OFF status of the air feeding button 5. The controller 22 is further connected to the pressure sensor 7 and receives a signal indicative of the pressure of the air enclosed in the air tube AT1.

Further, a driver 26 for driving the compressor 6 is connected to the controller 22, and another driver 23 for controlling the operation of the main valve 3 is connected to the controller 22.

The controller 22 detects the pressure of the air enclosed in the air tube AT1 based on the signal transmitted from the pressure sensor 7, and controls the driver 26 to drive the compressor 6 to maintain the air pressure in the air tube AT1 within a predetermined range about the value set by the pressure setting dial 8. Further, the controller 22 controls the driver 23 to open or close the main valve 3, in response to the operation of the air feeding switch 5.

The operation of the air feeding device 110 will be described in detail.

The controller 22 receives the data representing the pressure set through the pressure setting button 8, and then determines upper and lower limits UL and LL defining a predetermined range about the set pressure. If the pressure of the air tube AT1 is lower than the upper limit UL, the controller 22 controls the driver 26 to operate the compressor 6. If the air feeding button 5 is not depressed, the controller 22 controls the driver 23 so as to keep closing the main valve 3. Thus, the pressure of the air in the air tube AT1 increases unless the pressure is lower than the set pressure.

When the pressure reaches the upper limit UL, then the controller 22 controls the driver 26 to stop driving the compressor 26. Then, due to leak, the pressure gradually decreases. The controller 22 controls the driver 26 not to start driving the compressor 26 until the pressure reaches the lower limit LL. When the pressure reaches the lower limit LL, then the controller 22 controls the driver 26 to start driving the compressor 26 to increase the pressure. With this operation, if the main valve 3 remains closed, the air pressure in the air tube AT1 maintained within the range defined by the upper and lower limits UL and LL.

It should be noted that since the controller 22 first determines the upper and lower limits UL and LL, and controls the driver 26 by comparing the detected pressure with the upper and lower limits UL and LL depending on whether the pressure is increasing or decreasing, a so-called hunting phenomenon (i.e., repetition of turning ON and OFF) can be avoided.

After the pressure in the air tube AT1 exceeds the lower limit LL, it is possible to discharge the air by operating the air feeding button 5. Specifically, when an operator depresses the air feeding button 5, the controller 22 controls the driver 23 to open the main valve 3. Then, the air flows through the air tube AT2, and is discharged from the outlet 4. As described above, the air discharged from the outlet 4 is introduced, by the connection tube 16, to the forceps channel 18 of the endoscope 20.

FIGS. 3A through 3D show a graph illustrating a relationship between the changes of the pressure in the air tube AT1, turning ON and OFF of the compressor 6, open and close status of the main valve 3, and the air discharging status.

Initially, the controller 22 controls the driver 26 to drive the compressor 6, and accordingly, the pressure in the air tube AT1 increases (time T0–T1). As described above, until the air pressure reaches the upper limit (i.e., Level 1 in FIG. 3A), the compressor 6 operates. When the pressure reaches the upper limit (Level 1) at time T1, the controller 22 controls the driver 26 to turn OFF the compressor 6. Then, due to leak, the pressure decreases (from time T1). When the pressure decreases and reaches the lower limit (i.e., Level 2 in FIG. 3A), the controller 22 controls the driver 26 to drive the compressor 6 to increase the pressure at T2. Similar to the above, when the pressure reaches Level 1, the compressor 6 is turned OFF (T3).

In this example, the air feeding button 5 is depressed at time T4. In response to the depression of the air feeding button 5, controller 22 controls the driver 23 to open the main valve 3 (see FIG. 3C), and accordingly, the air is discharged from the outlet 4 (see FIG. 3D), and the pressure in the tube AT1 steeply decreases (see FIG. 3A). Since the pressure was lower than Level 2 at T4, the compressor 6 is turned ON (see FIG. 3B), and therefore, the pressure starts increasing again.

If the pressure reaches Level 1 (at time T5), the compressor 6 is turned OFF, and the pressure decreases due to the leak. If the pressure reaches Level 2 (at T6), the compressor 6 is turned ON again.

If the operator operates the pressure setting dial 8 to raise the pressure, the controller 22 sets the upper limit UL to Level 3, and the lower limit LL to Level 4. In this case, the controller 22 controls the driver 26 to keep driving the compressor 6 until the pressure reaches Level 3 (at time T7).

From T7, the pressure decreases due to the leak. If the air feed button 5 is depressed at T8, the mail valve 3 is opened (see FIG. 3C) and the air is discharged from the outlet 4 (see FIG. 3D), the pressure decreases steeply (see FIG. 3A) and the compressor 6 is turned ON (see FIG. 3B).

If it is assumed that the temperature is unchanged, in accordance with Boyle's law, the following relationship is satisfied.

$$Ve \times Pe = Vo \times Po = \text{constant}$$

where, Ve is a volume of the sealed space (i.e., the air tube AT1), Pe is the pressure of the air tube AT1, Vo is a volume after status of the air has been changed, and Po is the pressure after the status of the air has been changed. In this case, Ve is constant. Vo corresponds to the pressure of the discharged air. Po is the pressure of the discharged air, and which is considered to be the atmospheric pressure, and is constant. Accordingly, in order to increase the pressure of the discharged air, Pe should be increased.

As described above, according to the first embodiment, the pressure of the air in the sealed space (i.e., the air tube AT1) is increased in order to obtain sufficient discharging pressure. Therefore, if the compressor 6 is capable of increasing the pressure of the air in the sealed space, the amount of air flow need not be large. That is, only by increasing torque of the compressor, a sufficient discharging pressure is obtained, and it is not necessary to make a size of a pipe relatively large for allowing a large amount of air to flow therein. Therefore, a relatively small compressor can be used, which may not require a large current consumption.

Further, since only by controlling the pressure of the sealed space, a desired discharging pressure is obtained, and since the air is finally discharged to atmospheric air, a difference between the pressure in the sealed space and the atmospheric air determines the discharging pressure. Since the difference between the pressure in the sealed space and the atmospheric air can be made sufficiently small, the pressure of the discharged air can be controlled minutely.

Furthermore, according to the first embodiment, when the pressure of the sealed space has reached the upper limit UL, the compressor 6 is turned OFF. Thus, the noise generated by the compressor 6 is stopped while the compressor 6 is turned OFF. Further, since the compressor 6 according to the first embodiment can be made small, even when the compressor 6 is turned ON, the noise is relatively low in comparison with the conventional air feeding system.

Still further, since the display system is coupled to the endoscope, the diagnosis of human organs can be made with monitoring the subjected organs.

[Second Embodiment]

Figure 4:
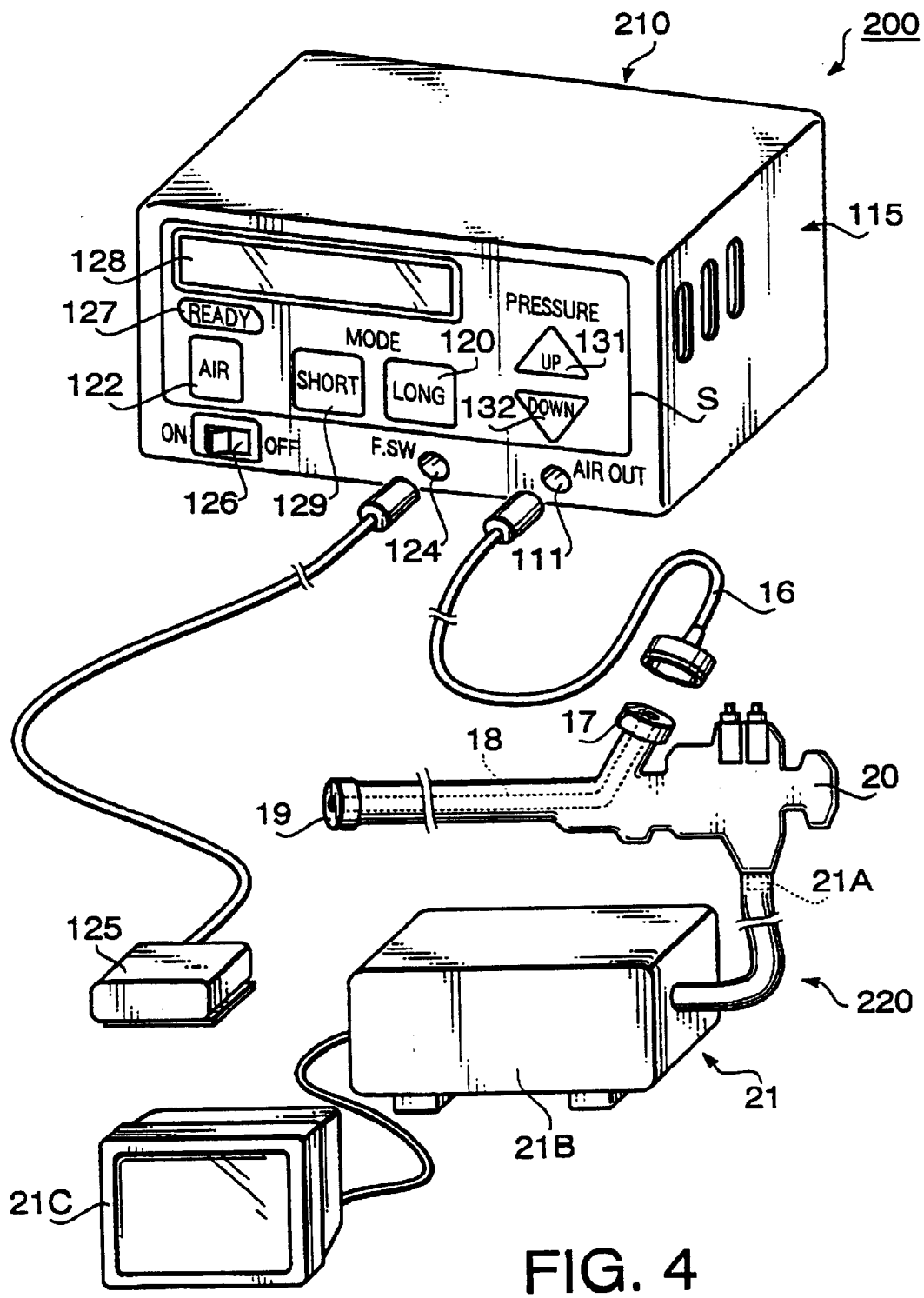

FIG. 4 schematically shows an entire air feeding system 200 according to a second embodiment of the invention.

The endoscope system 200 is provided with an air feeding device 210, and an endoscope system 220. It should be noted that the endoscope system 220 is similar to the endoscope system 120 shown in FIG. 1.

The air feeding device 210 has a casing 115, on which an operation panel S, a main switch 126, connection ports 111 and 124 are provided.

The main switch 126 is a switch for power ON the electrical circuits of the air feeding system 210.

On the operation panel S, an air feeding switch 122 is provided. The air feeding switch 122 is for discharging the air enclosed in a sealed space, which is formed inside the air feeding device 210, to outside thereof. That is, when the air feeding switch 122 is operated, the air is discharged from the connection port 111.

Further, on the operation panel S, a stand-by lamp 127, and an indicator 128 are provided. The stand-by lamp 127 is lit when the pressure has reached a predetermined pressure to indicate discharging of the air is ready. The indicator 128 displays, by numerals, a set pressure of the air.

Furthermore, on the operation panel S, a short pulse switch 129, a long pulse switch 130, an UP switch 131 and a DOWN switch 132 are provided.

The short pulse switch 129 is used when the air is to be discharged for a relatively shorter period of time. The long pulse switch 131 is a switch for discharging the air for a relatively longer period of time. In this embodiment, when the short pulse switch 129 is depressed, the air is discharged for 60 msec. (mili-seconds), while when the long pulse switch 130 is depressed, the air is discharged for one second. The UP and DOWN switches 131 and 132 are used for setting the pressure of the discharged air.

The endoscope system 220 includes an endoscope 20 and an image processor 21. The endoscope 20 is formed with a forceps channel 18. In this system, the air discharged from the air feeding device 210 is introduced in and flows through the forceps channel 18. In order to introduce the air from the air feeding device 210 to the forceps channel 18, a connection tube 16 is used. An end of the connection tube 16 is connected to the air discharging port 111 of the air feeding device 210, and the other end of the connection tube 16 is connected to the inlet 17 of the forceps channel 18. Thus, the air discharged from the air feeding device 210 flows in the connection tube 16 and the forceps channel 18, and discharged out of an outlet 19 of the forceps channel 18.

The image processor 21 includes an imaging device 21A for capturing an optical image formed by the endoscope 20 and output an image signal, an signal processing device 21B for processing the image signal, and a display 21C for display an image in accordance with the image signal output from the image processing device 21B.

To the connector 124, a cable of a foot switch 125 is connected.

Figure 5:
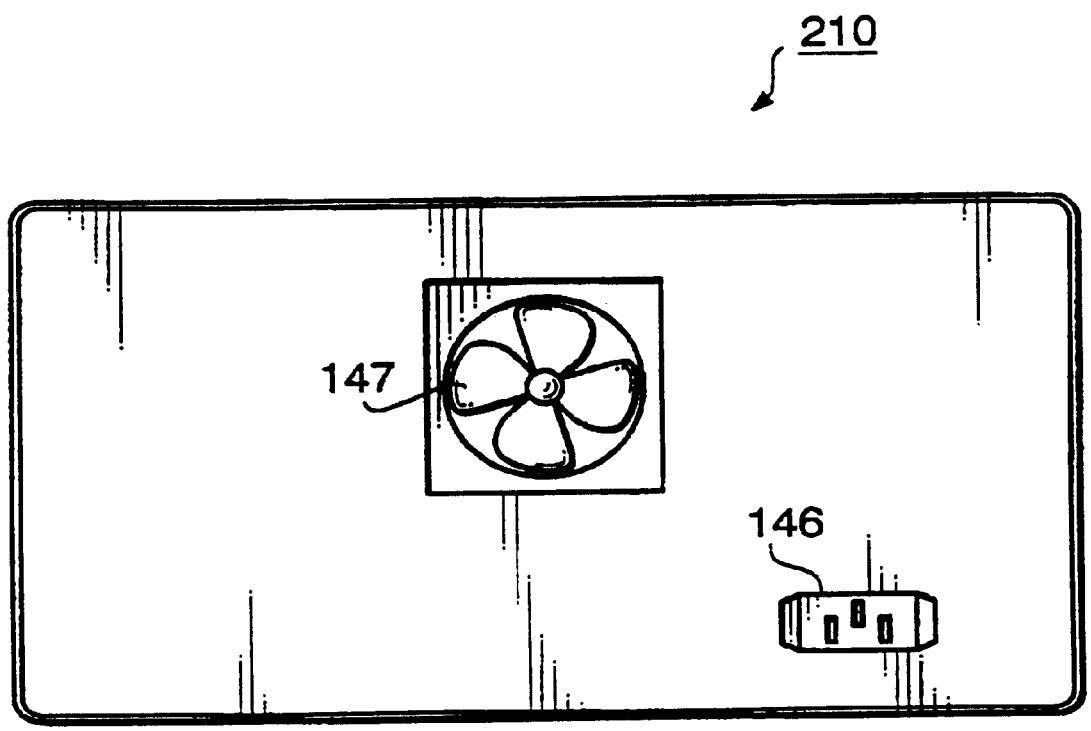

FIG. 5 is a rear view of the air feeding device 210. As shown in FIG. 5, a DC fan 147 for cooling the device 210, and an AC inlet 146 to be connected to a commercial electric power source are provided.

Figure 6:
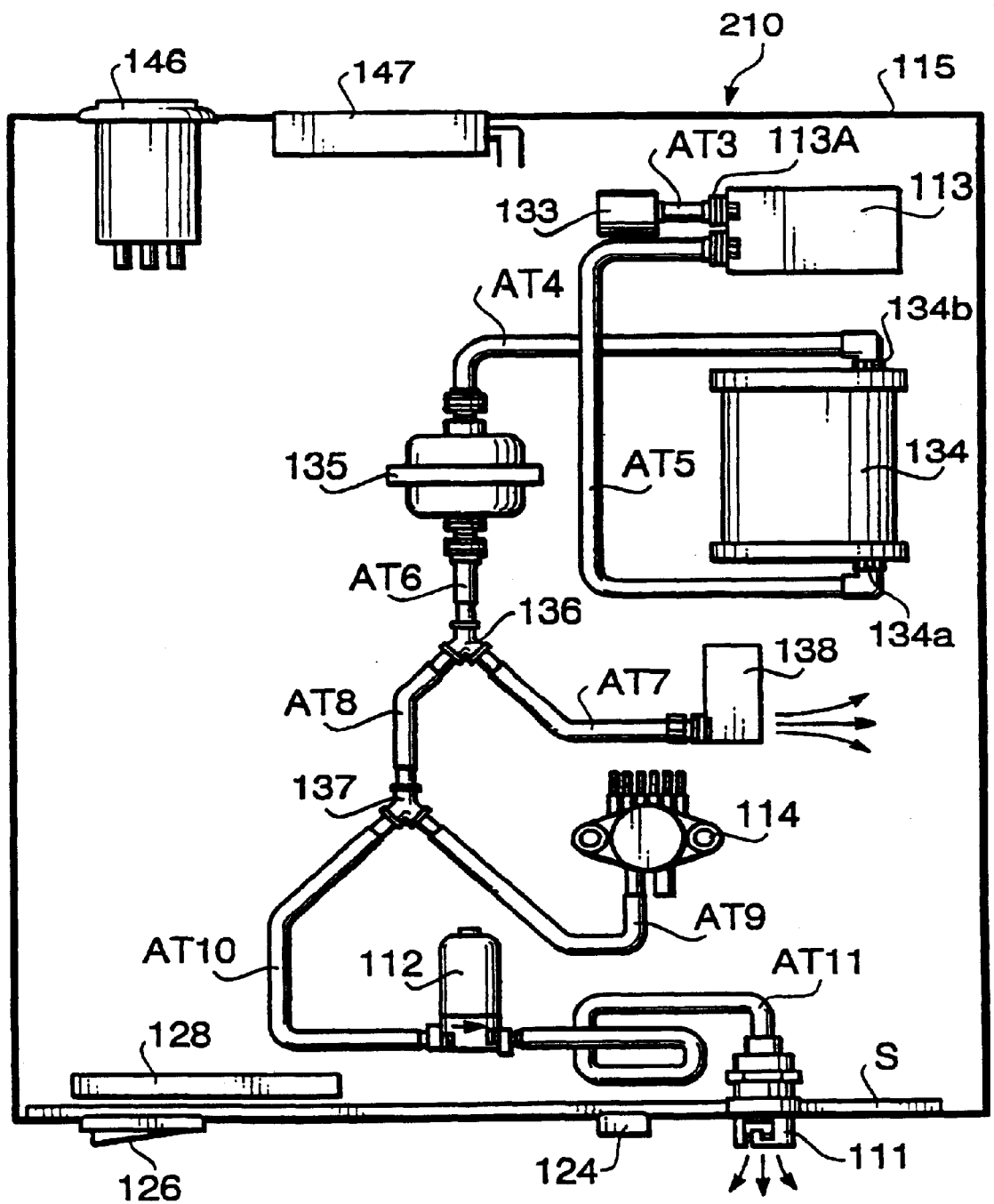

FIG. 6 schematically shows an arrangement of main elements inside the air feeding device 210, when viewed from the top. As described above, on a wall of the casing 115, the AC inlet 146, the DC fan 147, the power switch 126, the operation panel S provided with the indication unit 128, the outlet 111, and the connector 124 are provided.

Inside the casing 115, a sealed space for feeding the air is formed. Specifically, the sealed space is formed by: a compressor 113, an air tube AT5, an air tank 134, an air tube AT4, an air filter 135, an air tube AT6, a Y-joint 136, an air tube AT7, a pressure control valve 138, an air tube AT8, a Y-joint 137, an air tube AT9, a pressure sensor 114, an air tube AT10, and a discharging valve 112. The air enclosed in the sealed space is discharged from the outlet 111 via the air tube AT11.

The sealed space between the air filter 135 to the discharging valve 112 is branched by the joint 136 and the air tube AT7 towards the pressure control valve 138, and by the joint 137 and the air tube AT9 towards the pressure sensor 114. It should be noted that the air tubes AT6, AT7 and AT8 communicate with each other through the joint 136. Further, the air tubes AT9, AT8 and AT10 communicate with each other through the joint 137.

The air enclosed in the sealed space is discharged when the pressure is adjusted, and the air is fed to the human cavity. The pressure control valve 138 is used for the former purpose, i.e., the pressure control valve 138 only opens when the pressure of the air in the sealed space is reduced. The discharging valve 112 is usually closed, and is opened only when the air feeding switch 122 or the foot switch 125 are operated.

In the second embodiment, a silencer 133 is provided for reducing noise when the compressor 113 operates. Specifically, the silencer 133 is coupled to the air intake 113A of the compressor 113 via the air tube AT3. When the compressor 113 starts operating, the air is introduced, via the silencer 133 and the air tube AT3, from the intake 113A of the compressor 113, and fed into the sealed space through an outlet 113B of the compressor 113, thereby the pressure in the sealed space is increased.

The air tank 134 is provided for enlarging the volume of the sealed space. The volume of the air tank 134 is much larger than the sum of the volumes of the air tubes AT4 through AT10. The air tank 134 is provided with connectors 134a and 134b on opposite surfaces, respectively, and the air tube AT5, which connects the outlet of the compressor 113, is connected to the connector 134a which is located farther from the compressor 113 than the connector 134a is.

The air filter 135 removes the dust existing in the sealed space.

The pressure inside the sealed space is measured by the pressure sensor 114.

The pressure control valve 138 is driven to adjust the pressure in the sealed space. Specifically, if the pressure inside the sealed space, which is detected by the pressure sensor 114, is lower than the set pressure, the compressor 113 is driven and the pressure control valve 138 is closed. If the pressure inside the sealed space is higher than the set pressure, the compressor 113 stops operating, and the pressure control valve 138 is opened. If the pressure inside the sealed space coincides with the set pressure, the compressor 113 does not operate, and the pressure control valve 138 is closed.

The discharging valve 112 operates in response to operation of the air feeding switch 122 or the foot switch 125. When the discharging valve 112 opens, the air is discharged from the outlet 111 via the air tube AT11.

Figure 7:
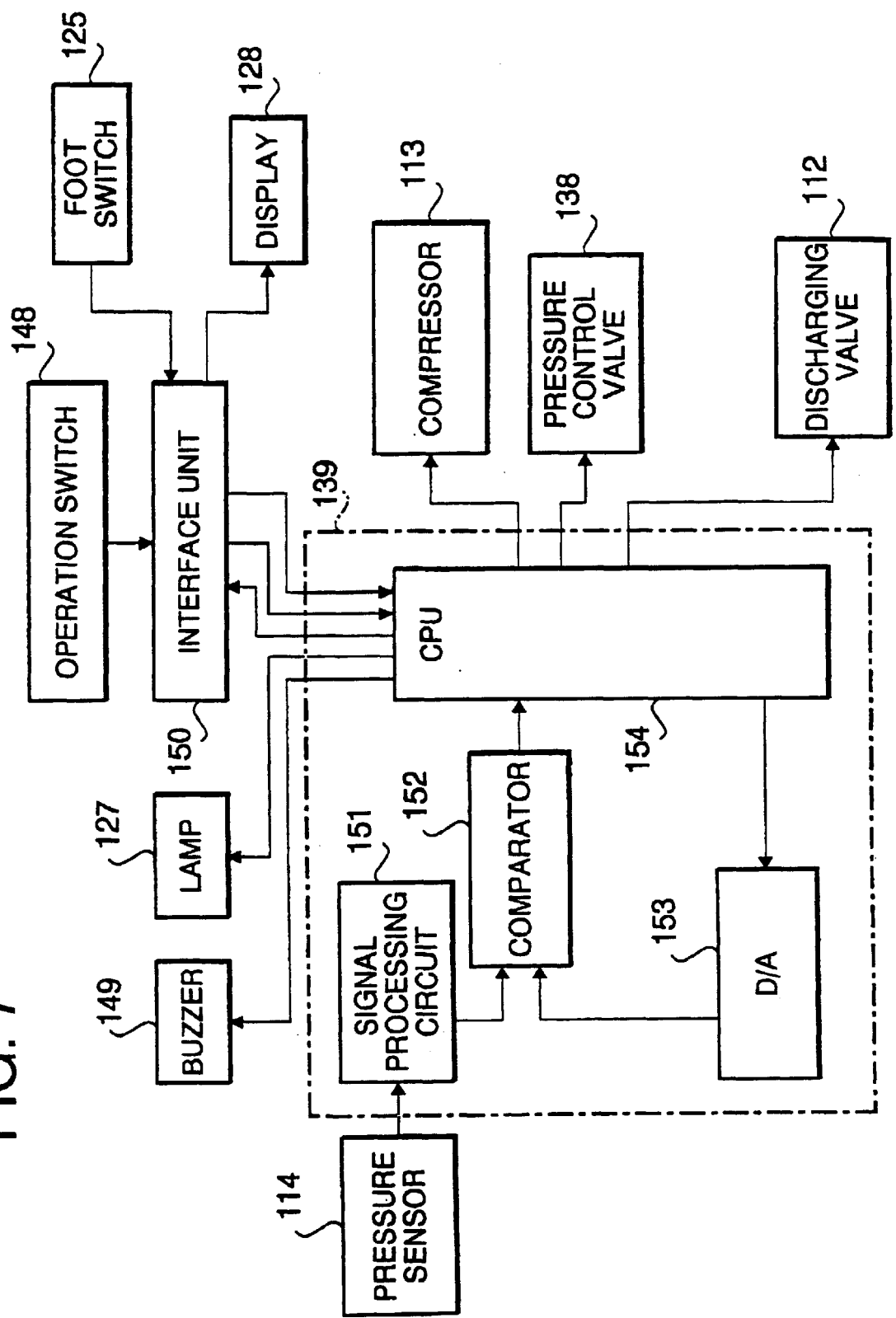
FIG. 7 is a block diagram illustrating a control system of the air feeding device according to the second embodiment.

FIG. 7 is a block diagram illustrating a control system of the air feeding device 210 according to the second embodiment. The control system is provided with a controller 139, which includes a signal processing circuit 51, a comparator 152, a D/A converter 153, and a CPU (Central Processing Unit) 154. The controller 139 controls the operation of the entire system of the air feeding device 210. The CPU 154 outputs driving signals to the piezo-electric buzzer 149, a lamp 126, the compressor 113, the pressure control valve 138, and the discharging valve 112.

An operation switch unit 148 outputs predetermined signals in response to the operation of the air feeding switch 122, the short pulse switch 129, the long pulse switch 130, the UP switch 131 and the DOWN switch 132. The signals generated by the operation switch unit 148 and the foot switch 125 are transmitted to the CPU 154 via an interface unit 150. The interface unit 150 applies predetermined signal processing/converting operations and outputs signals suitable to be processed by the CPU 150. The interface unit 150 determines the currently set pressure in accordance with the signals generated in response to the operation of the UP and DOWN switches 131 and 132, and controls the display unit 128 to display the same.

The signal output by the pressure sensor 114 is input into the signal processing circuit 151, and a predetermined signal processing operation (e.g., noise reduction) is applied. Then, the processed signal is input in the comparator 152. On the other hand, the signal representing the currently set pressure, which is set by the UP and DOWN switches 131 and 132 is transmitted from the CPU 154 to the D/A converter 153 which output an analog voltage value. The analog voltage value is input to the other input port of the comparator 152.

The comparator 152 outputs the signal indicating a relationship between the voltage output by the signal processing circuit 151 and the voltage output by the D/A converter 153. The CPU 154 judges whether the current pressure in the sealed space is equal to the set pressure.

It should be noted that, if the voltages compared by the comparator 152 are different but substantially equal, the operation of the compressor 113, and open/close of the pressure control valve 138 may repeats within a relatively short period of time (i.e., a so-called hunting phenomenon). In order to avoid such a situation, the comparator 152 is constituted to output a LOW or HIGH signal when the difference between the voltages applied by the signal processing circuit 151 and the D/A converter 152 exceeds a predetermined value.

The piezo-electric buzzer 149 is driven to buzz in accordance with the switch operations. The lamp 127 is lit when the air feeding device 210 is in the stand-by condition.

Through the AC inlet 146, the main switch 126, the electric power is supplied to a power circuit (not shown), from which the electrical power is supplied to the display unit 128, the pressure sensor 114, the CPU 154, the compressor 113, the pressure control valve 138, and the discharging valve 112.

Figure 8:
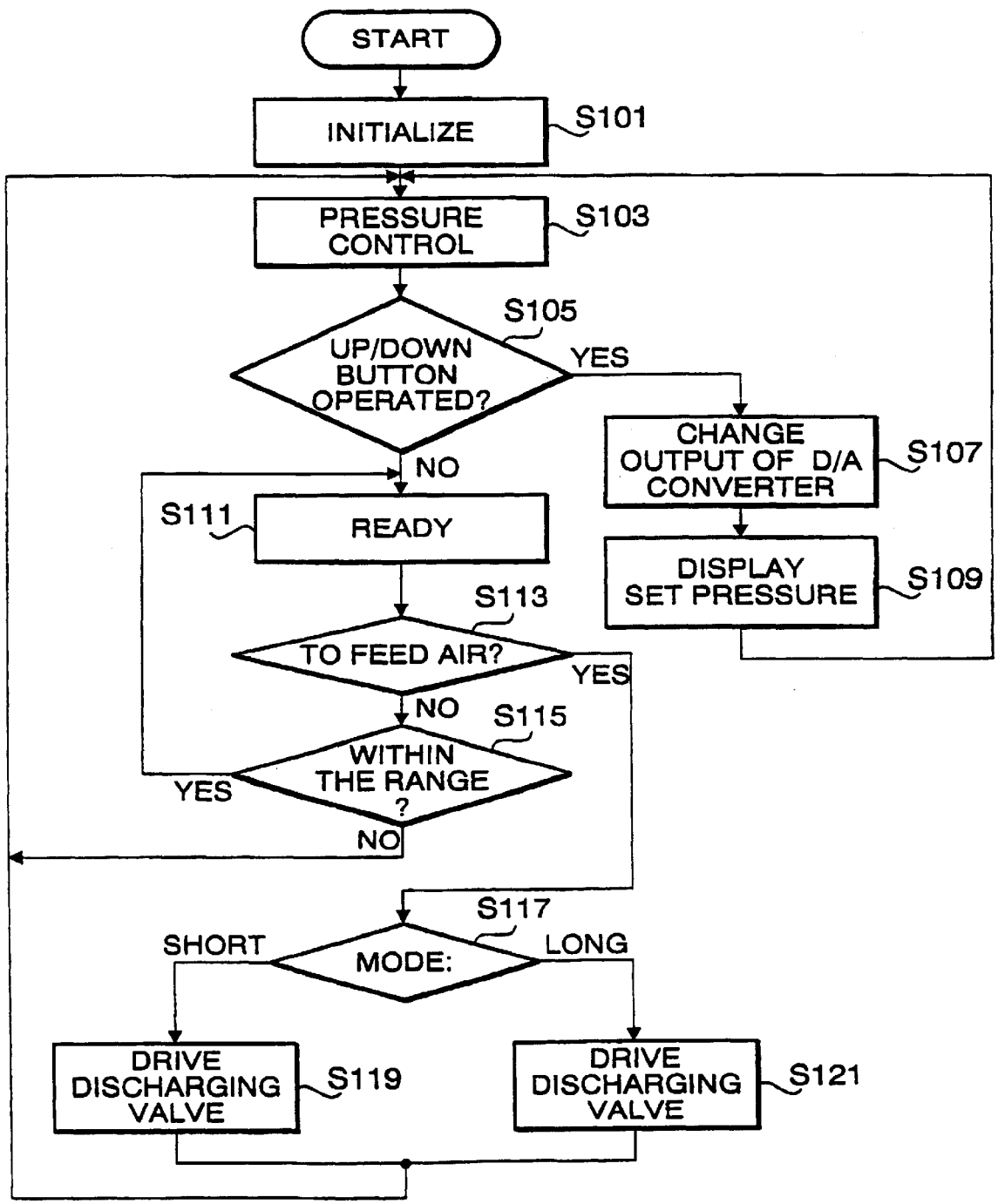
FIG. 8 is a flowchart illustrating the operation of the air feeding device.

FIG. 8 is a flowchart illustrating the operation of the air feeding device 210. The procedure shown in FIG. 8 starts when the main switch 126 is turned ON.

In S101, an initialization process is performed. In the initialization process, the pressure of the sealed space is set to a default value. The set pressure value is displayed on the display unit 128. In S103, a pressure control operation is performed. The pressure control operation will be described later in detail.

In S105, it is judged whether the UP switch or DOWN switch is operated. If the UP switch 131 or the DOWN switch 132 is operated (S105: YES), the output voltage of the D/A converter 153 is also changed (S107), and the changed value (pressure) is displayed on the display unit 128 (S109).Thereafter, control returns to S103.

If both the UP switch 131 and the DOWN switch 132 are not operated (s105: NO), control goes to S111.

At S111, if the lamp 27 is lit to indicate that the air feeding device 210 is ready to operate. In S113, it is judged whether the foot switch 125 or the discharging switch 122 is operated. If the either of the foot switch 125 and the discharging switch 122 is not operated (S113: NO), it is judged whether the pressure in the sealed space is within a predetermined range about the set pressure. If the pressure in the sealed space is within the predetermined range, control returns to S111 to keep the lamp 127 to be lit. If the pressure in the sealed space is out of the predetermined range (S111: NO), control goes to S103 to executed the pressure control operation.

If the air feeding switch 122 or the foot switch 125 is operated (S113: YES) when the steps of S111, S113 and S115 are repeated, which of the short pulse mode and the long pulse mode is selected is judged in S117.

If the short pulse mode is selected, control goes to S119, where the discharging valve 112 is driven such that the air is discharged for a first predetermined period (e.g., 60 msec).

If the long pulse mode is selected, control goes to S121, where the discharging valve 112 is driven such that the air is discharged for a second predetermined period (e.g., one second).

After the air is discharged in S119 or S121, control returns to S103, and the pressure control operation is executed in S103.

Figure 9:
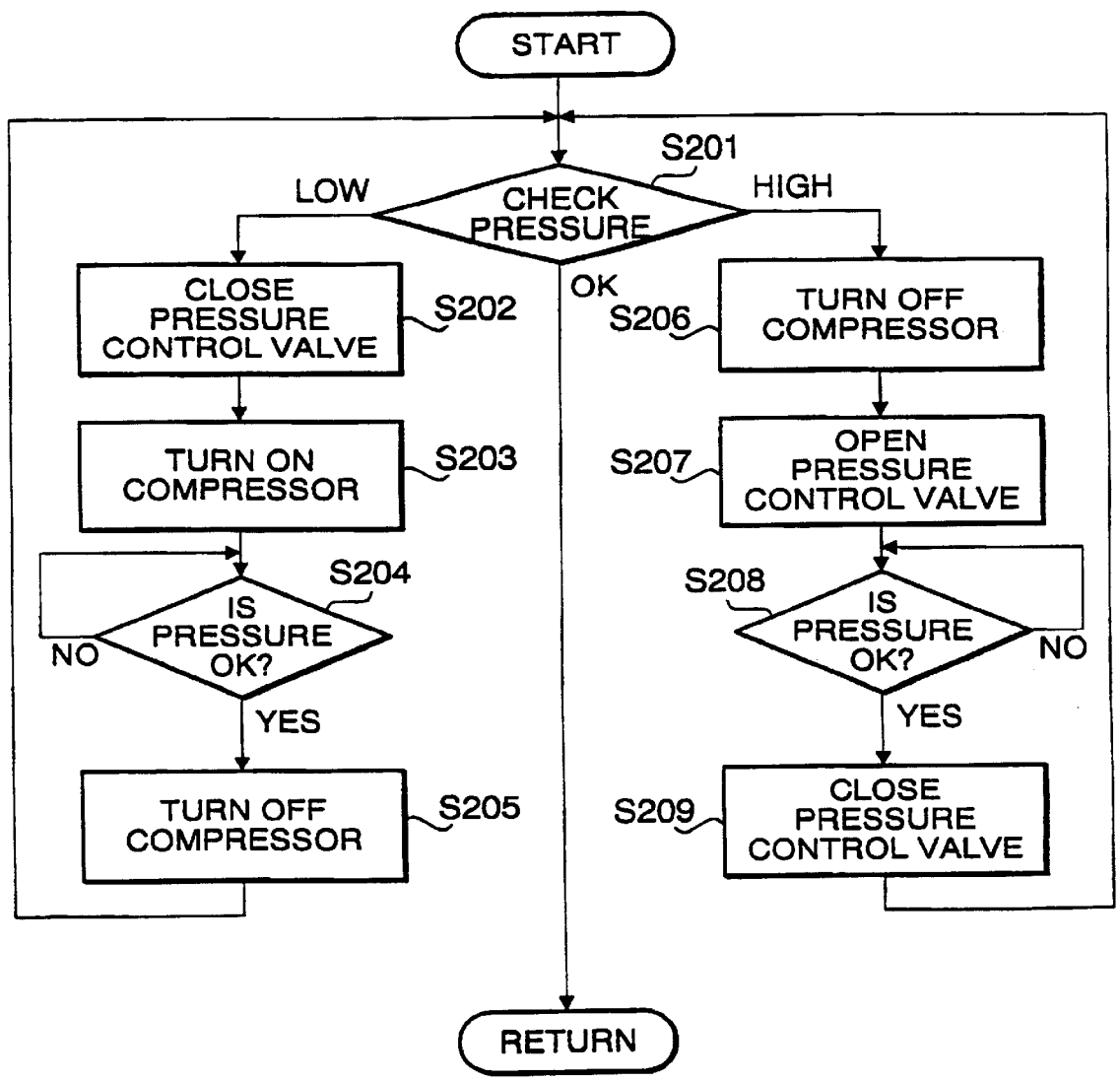
FIG. 9 is a flowchart illustrating the pressure control operation.

FIG. 9 is a flowchart illustrating the pressure control operation in detail.

In S201, it is judged whether the pressure in the sealed space and detected by the pressure sensor 114 is out of the predetermined pressure range. If the pressure in the sealed space is within the predetermined pressure range, control exits from the procedure.

If the pressure in the sealed space is lower than the lower limit of the predetermined range, control goes to S202. In this case, the pressure control valve 138 is closed (S202), and the compressor 113 is controlled to start operating (S103). In S204, the pressure is checked, and until the pressure is within the predetermined range, the compressor is kept operating. When the pressure is within the range, the compressor 113 is turned OFF, and control returns to S201.

If the pressure in the sealed space is higher than the upper limit of the predetermined range, control goes to S206. In this case, the compressor 113 is turned OFF, and the pressure control valve 138 is opened (S207). In S208, the pressure is checked, and until the pressure is within the predetermined range, the pressure control valve 113 remain opened. When the pressure is within the range, the pressure control valve 113 is closed, and control returns to S201.

FIGS. 10A through 10E show a graph illustrating a relationship between the changes of the pressure in the sealed space, turning ON and OFF of the compressor 113, open and close status of the pressure control valve 138 and the discharging valve 112, and the air discharging status.

Initially, the CPU 154 controls the compressor 113 to operate, and accordingly, the pressure in the sealed space increases (time T0–T1). Until the air pressure reaches the upper limit (i.e., Level 1 in FIG. 10A), the compressor 113 is kept operating. When the pressure reaches the upper limit (Level 1) at time T1, the CPU 154 turns OFF the compressor 113. Then, the pressure is maintained at Level 1 (from time T1).

Figure 10:
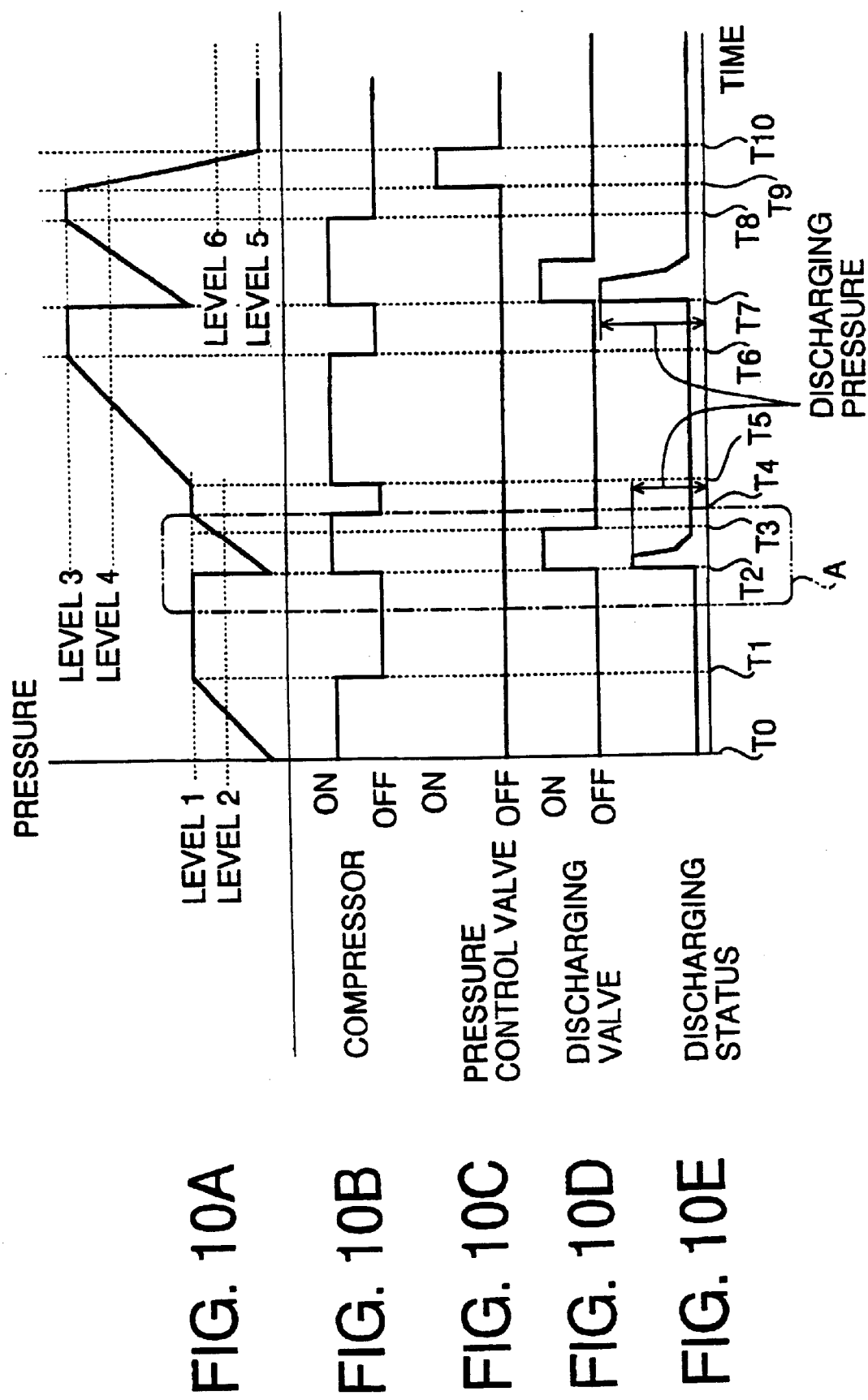
FIGS. 10A through 10E show a graph illustrating a relationship between the changes of the pressure in the sealed space, turning ON and OFF of the compressor, open and close status of the pressure control valve and the discharging valve, and the air discharging status.

In this example, the air feeding switch 122 or foot switch 125 is operated at time T2. In this example, the discharging air mode is set to the short pulse mode, and the discharging period is 60 msec. As shown in FIG. 10D, in response to the operation of the air feeding switch 122 or the foot switch 125, the CPU 154 controls the discharging valve 112 (see FIG. 10C) for 60 msec. (T2–T3), and accordingly, the air is discharged from the outlet 111 (see FIG. 10E), and the pressure steeply decreases (see FIG. 10A). Since the pressure was lower than Level 2 at T2, the compressor 113 is turned ON (see FIG. 10B), and therefore, the pressure starts increasing again (see FIG. 10A).

The discharging valve 112 is closed at time T3, and when the pressure reaches Level 1 (at time T5), the compressor 113 is turned OFF.

If the set pressure is changed higher at T5, the upper and lower limits, i.e., Level 3 and Level 4 are defined. Then, the compressor 113 is turned ON since Level 1 is lower than Level 4, and when the pressure reaches Level 3, the compressor 113 is turned OFF (at T6).

If the air feeding switch 122 or the foot switch 125 is operated at T7, the pressure steeply decreases (see FIG. 10A) and accordingly, the compressor 113 is turned ON. When the pressure reaches Level 3 at T8, the compressor 113 is turned OFF.

If the set pressure is changed lower at T9, the upper and lower limits, i.e., Level 5 and Level 6 are defined. Further, in order to decrease the pressure in the sealed space, the pressure control valve 138 is opened at T9 (see FIG. 10C). Then, the pressure decrease, and when the pressure reaches Level 5 (at T10), the pressure control valve 138 is closed (see FIG. 10C).

Figure 11:
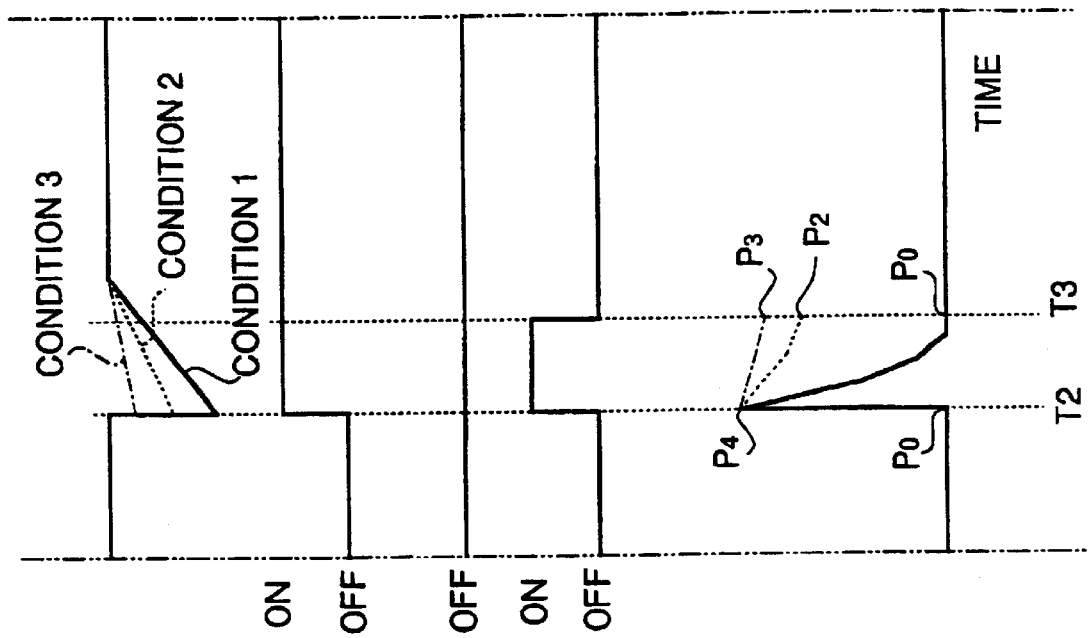
FIGS. 11A–11E are enlarged views of portion A of FIGS. 10A–10E.

FIGS. 11A–11E are enlarged views of portion A of FIGS. 10A–10E. In FIGS. 11A and 11E, the solid line represents a change under condition one in which the capacity of the air tank 134 is relatively small, the broken line represents a change under condition two in which the capacity of the air tank 134 is intermediate, and the dotted line represents a change under condition three in which the capacity of the air tank 134 is relatively large.

When the discharging valve 112 is opened at T2, the pressure of the discharged air increases from P0 to P4 in FIG. 11E. At T3, the discharging valve 112 is closed and therefore the pressure is decreased to P0 in FIG. 1E.

Within the interval between time T2 to time T3, the condition of the discharged air would be different depending on the capacity of the air tank 134.

When the capacity of the air tank 134 is relatively small (condition ONE), as shown in FIG. 1E, the pressure of the discharged air steeply decreases, and reaches P0.

If the capacity of the air tank 134 is intermediate (condition TWO), as shown in FIG. 1E, the pressure of the discharged air decreases to P2 at time T3.

If the capacity of the air tank 134 is relatively large (condition THREE), the pressure of the discharged air decreases to P3, which is greater than P2, at time T3.

Thus, if the capacity of the air tank 134 is relatively large, the pressure is substantially unchanged or changed little during the air discharging period.

A relationship between the pressure of the discharging air and the volume of the sealed space will be described below. In order to simplify the explanation, it is assumed that the pressure of the air in the sealed space is constant, and the volume of the sealed space is substantially equal to the volume of the air tank 134.

The relationship between the volume and pressure, which is well-known as the Boyle's law and described before, is expressed as follows.

$$P \times V = \text{constant}$$

where P represents the pressure, V represent the volume, and it is assumed that the temperature is unchanged.

If the air in the sealed space is completely discharged, the volume of the air after it is discharged from the sealed space is equal to the total amount of air flow discharged from the outlet 19 of the forceps channel 18.

If the pressure and volume before discharged are represented by P0 and V0, and those after discharged are represented by P1 and V1, the following relationship is satisfied.

$$P0 \times V0 = P1 \times V1 \quad P1 \times Q \times T$$

where, Q is an amount of air discharged from the outlet 19 per a unit time period, and T is time.

It is experimentally known that the pressure of the discharged air and the total amount Q×T have a linear relationship. If the pressure of the discharged air is made higher, the volume V1 is becomes large. Since the pressure P0 is constant, and the pressure P1 equals to the atmospheric pressure, it is understood that the pressure P1 of the air being discharged and the volume V0 have a linear relationship.

Due to the above relationship between the pressure of the air being discharged and the volume V0, in order to discharge the air at a relatively high pressure for a certain period of time, the volume V0 should be made sufficiently large. In other words, in order to discharge the air for a predetermined period of time at various discharging pressures, the capacity of the air tank 34 should be sufficiently large.

As an example, the volume V0 of the sealed space in order to discharge the air, whose discharging pressure is 10 mmHg, for one second is calculated. The total flowing amount of the discharged air Q×T is determined by an empirical formula, and the value (i.e., the discharged amount) is 65 cc. If it is assumed that the pressure P0 in the sealed space is 1.5 times of the atmospheric pressure P1, the volume V0 of the sealed space is calculated to be approximately 40 cc.

If the decrement of the volume of the air after some of the air has been discharged is to be suppressed to 10% or less, the air tank 34 should have 10 times as large as the volume V0, i.e., 400 cc. It is preferable to multiply a coefficient, and thus the capacity may be calculated as 1000 cc.

As described above, according to the second embodiment, by turning ON/OFF the compressor 113, and turning ON/OFF the pressure control valve 138, the pressure of the air in the sealed space can be adjusted to obtain a desired discharging pressure. Further, in response to the changed setting, the pressure of the air in the sealed space can be adjusted immediately, and accordingly, the discharging pressure can also be adjusted.

Furthermore, since the air is discharged from the sealed space, the air can be discharged as a pulsing (i.e., an intermittent) flow. Since the relatively large air tank 134 is provided, the air can be discharged for a certain period of time at a predetermined pressure.

Still further, according to the second embodiment, since the compressor 113 is not operated continuously, the continuous noise can be avoided, and power consumption can be reduced.

As shown in FIG. 6, the air tube AT5 which is connected to the compressor 113 is connected to the connection port 34a which is remote from the compressor 113. Accordingly, the vibration of the compressor 113 may be attenuated and may not be transmitted to the air tank 134. Further, according to the second embodiment, it is not necessary to feed a large amount of air to the sealed space, and therefore a relatively small compressor 113 can be used.

Still further, according to the second embodiment, it is possible to feed the air by operating the foot switch 125. Therefore, it is easy to handle the endoscope when the air is to be struck on the organs with operating the endoscope.

The short pules switch 129 is used for discharging the air for 60 msec. and the long pulse switch 130 is used for discharging the air for one second. The invention should not be limited to these values, and the periods of time can be set to other values. Optionally or alternatively, the periods of time maybe made changeable, for example, may be made selectable from among a plurality of values.

Furthermore, the air tank 134 may be arranged between the air filter 135 and the discharging valve 112. That is, the air tank 134 may be arranged between the air tubes AT6 and AT8, or between the air tubes AT8 and AT10.

[Third Embodiment]

FIG. 12 schematically shows an entire air feeding system 300 according to a third embodiment of the invention.

The endoscope system 300 is provided with an air feeding device 310, and an endoscope system 320. It should be noted that the endoscope system 320 is similar to the endoscope system 120 shown in FIG. 1.

The air feeding device 310 is substantially similar to the air feeding device 210 according to the second embodiment (shown in FIG. 4). Only the difference is that the air feeding device 310 according to the third embodiment is provided with an enter switch 223 on the operation panel S.

The enter switch 223 is used for adjusting the pressure of the sealed space. That is, when the enter switch 223 is ON, the pressure of the sealed space is adjusted to meet the set pressure.

FIG. 13 is a block diagram showing the control system of the air feeding device 310. The control system shown in FIG. 13 is similar to the control system shown in FIG. 7 according to the second embodiment except that the enter switch 223 is connected to the interface unit 150, and a memory 154M inside the CPU 154 is explicitly indicated. The memory 154M is used for temporarily storing the output of the comparator 152 as comparison data.

Similar to the second embodiment, the pressure in the sealed space is detected, and in accordance with the detected pressure and the set pressure, the compressor 113, the pressure control valve 138 are driven to maintain the pressure within a range defined with reference to the set pressure. In the second embodiment, when the operator changes the set pressure, the changed value is immediately applied, and the pressure in the sealed space is changed in response to the newly set pressure.

In the third embodiment, only when the enter switch 223 is ON, the newly set pressure is applied. Specifically, when the enter switch 223 is OFF, even if the operator changes the pressure, the changed value (i.e., the newly set value) is not reflected for controlling the compressor 113 and/or the pressure control valve 138. As described above, the pressure newly set or being set is temporarily stored in the memory 154M.

When the enter switch 223 is ON, the CPU 154 determines a new reference value corresponding to the data stored in the memory 154M, and transfers the new reference value data to the D/A converter 153. Thereafter, the CPU 154 drives the compressor 113 and/or the pressure control valve 138 to adjust the pressure by comparing the output of the signal processing circuit 151 with the output of the D/A converter 153 (i.e., the new reference value). It should be noted that the operation for adjusting the pressure is similar to that of the second embodiment.

FIG. 14 is a flowchart illustrating the reference data setting procedure executed by the CPU 154.

In S301, a predetermined reference value for adjusting the pressure in the sealed space is stored in the memory 154M.

At the same time, on the display 128, the initially set pressure is displayed.

In S302, a pressure control operation is performed. This operation is similar to that illustrated in the flowchart shown in FIG. 9.

In S303, it is judged whether the set pressure is changed. That is, if the UP switch 131 or the DOWN switch 132 is operated, the set pressure is changed. In the third embodiment, since the changed pressure is applied after operation of the enter switch 223, when the set pressure is being changed, the value of the pressure is displayed on the display device 128 together with a predetermined mark indicating that the displayed value has not yet been applied. The changed value is stored in the memory 154M (S304).

If the pressure is not changed (S303: NO), control goes to S305.

In S305, it is judged whether the enter switch 223 is operated. If the enter switch 223 has not yet been operated after the pressure value is changed, control skips S306, and accordingly, the reference value output to the D/A converter 153 is not changed. If the enter switch 223 is operated (S305: YES), then control goes to S306, where the CPU 154 determines a new reference value based on the data stored in the memory 154M, and the new reference value data is transmitted to the D/A converter 153.

As above, according to the third embodiment, when the UP switch or DOWN switch is operated to change the setting value, the changed value is not reflected for operating the compressor and/or the pressure control valve. Thus, unnecessary or unintentional performance can be avoided, and change of the set pressure can be done efficiently.

The present disclosure relates to the subject matters contained in Japanese Patent Applications No. HEI 10-188868, filed on Jul. 3, 1998, No. HEI 10-250145, filed on Sep. 3, 1998, No. HEI 10-258474, filed on Sep. 11, 1998, which are expressly incorporated herein by reference in their entireties.

What is claimed is:

1. An air feeding device for an endoscope system, comprising:
   an air compressor that compresses air and feeds the air into a sealed space;
   a pressure sensor that detects air pressure in said sealed space;
   a pressure setting device through which a pressure value in said sealed space to be adjusted is set;
   a pressure controller that turns said compressor ON and OFF in accordance with the air pressure detected by said pressure sensor and said pressure value set by said pressure setting device;
   a main valve, an inlet of said main value being connected to said sealed space, an inlet of said main valve being connected to an outlet of said air feeding device; and
   a control system that controls said main valve to selectively discharge air to said outlet for at least one of a predetermined period of time and in a pulsing manner.

2. The air feeding device according to claim 1, wherein said pressure controller includes a comparator which compares output of said pressure sensor with a reference value, and wherein said pressure controller turns ON or OFF said compressor depending on the comparison result of said comparator.

3. The air feeding device according to claim 1, wherein said reference value is determined based on said pressure value set by said pressure setting device.

4. The air feeding device according to claim 1,
   wherein said pressure controller defines first and second reference values based on said pressure value set by said pressure setting device, said first reference value being greater than said pressure value, said second reference value being less than said pressure value,
   wherein said pressure controller includes a comparator,
   wherein said pressure controller turns OFF said compressor if the pressure detected by said pressure sensor is increasing and the pressure detected by said pressure sensor reaches said first reference value, and
   wherein said pressure controller turns ON said compressor if the pressure detected by said pressure sensor is decreasing and the pressure detected by said pressure sensor reaches said second reference value.

5. An air feeding device for an endoscope system, comprising:
   an air compressor that compresses air and feeds the air into a sealed space;
   an air tank forming part of said sealed space;
   a pressure sensor that detects air pressure in said sealed space;
   a pressure setting device through which a pressure value in said sealed space to be adjusted is set;
   a pressure controlling valve that releases air in said sealed space;
   a pressure controller that turns said compressor ON and OFF and/or turns said pressure controlling valve ON and OFF in accordance with the air pressure detected by said pressure sensor and said pressure value set by said pressure setting device;
   an air feeding valve, an inlet of said air feeding valve being connected to said sealed space, an outlet of said air feeding valve being connected to an outlet of said air feeding device; and
   a discharge controller that controls said air feeding valve to selectively discharge air from said sealed space to said outlet for at least one of a predetermined period of time and in a pulsing manner.

6. The air feeding device according to claim 5, wherein said sealed space is defined as a space between said compressor and said air feeding valve, said air tank being arranged between said compressor and said air feeding valve, wherein said air feeding device further comprises tube members for connecting said compressor and said air tank, and for connecting said air tank and said air feeding valve.

7. The air feeding device according to claim 6, wherein a volume of said air tank is greater than a volume of said sealed space excluding the volume of said air tank.

8. The air feeding device according to claim 5, further provided with an air filter which is inserted within said sealed space.

9. The air feeding device according to claim 5,
   wherein said pressure controller defines first and second reference values based on said pressure value set by said pressure setting device, said first reference value being greater than said pressure value, said second reference value being less than said pressure value,
   wherein said pressure controller turns OFF said compressor if the pressure detected by said pressure sensor is greater than said first reference value, and
   wherein said pressure controller turns ON said compressor if the pressure detected by said pressure sensor is less than said second reference value.

10. The air feeding device according to claim 5,
   wherein said pressure controller defines first and second reference values based on said pressure value set by said pressure setting device, said first reference value being greater than said pressure value, said second reference value being less than said pressure value,
   wherein said pressure controller controls said pressure control valve to open if the pressure detected by said pressure sensor is greater than said first reference value, and
   wherein said pressure controller controls said pressure control valve to close if the pressure detected by said pressure sensor is less than said second reference value.

11. An air feeding device for an endoscope system, comprising:
   an air compressor that compresses air and feeds the air into a sealed space;
   a pressure sensor that detects air pressure in said sealed space;
   a pressure controller that turn s said compressor ON and OFF in accordance with the air pressure detected by said pressure sensor and a predetermined pressure value ;

a main valve, an inlet of said main valve being connected to said sealed space, an outlet of said main valve being connected to an outlet of said air feeding device;

a main valve controller that controls said main valve to selectively discharge air to said outlet for at least one of a predetermined period of time and in a pulsing manner;

a pressure setting device through which a pressure value in said sealed space to be adjusted is set;

an enter switch that is manually operated to make the pressure value set by said setting device effective, wherein, when the pressure value is set by said pressure setting device and said enter switch is operated, said pressure controller controls said compressor in accordance with the air pressure detected by said pressure sensor and the pressure value set by said pressure setting device.

12. An air feeding device for an endoscope system, comprising:

an air compressor that compresses air and feeds the air into a sealed space;

an air tank forming part of said sealed space;

a pressure sensor that detects air pressure in said sealed space;

a pressure controlling valve that releases air in said sealed space;

a pressure controller that turns said compressor ON and OFF and/or turns said pressure controlling valve ON and OFF in accordance with the air pressure detected by said pressure sensor and a predetermined pressure value;

an air feeding valve, an inlet of said air feeding valve being connected to said sealed space, an outlet of said air feeding valve being connected to an outlet of said air feeding device;

an air feeding valve controller that controls said air feeding valve to selectively discharge air to said outlet for at least one of a predetermined period of time and in a pulsing manner;

a pressure setting device through which a pressure value in said sealed space to be adjusted is set; and an enter switch that is manually operated to make the pressure value set by said setting device effective, wherein, when the pressure value is set by said pressure setting device and said enter switch is operated, said pressure controller controls said compressor and said pressure controlling valve in accordance with the air pressure detected by said pressure sensor and the pressure value set by said pressure setting device.

13. The air feeding device according to claim 12, wherein said sealed space is defined as a space between said compressor and said air feeding valve, said air tank being arranged between said compressor and said air feeding valve, wherein said air feeding device further comprises tube members for connecting said compressor and said air tank, and for connecting said air tank and said air feeding valve.

14. The air feeding device according to claim 13, wherein a volume of said air tank is greater than a volume of said sealed space excluding the volume of said air tank.

15. The air feeding device according to claim 12, further provided with an air filter which is inserted within said sealed space.

16. The air feeding device according to claim 12, wherein said pressure controller defines first and second reference values based on said pressure value set by said pressure setting device, said first reference value being greater than said pressure value, said second reference value being less than said pressure value, wherein said pressure controller turns OFF said compressor if the pressure detected by said pressure sensor is greater than said first reference value, and wherein said pressure controller turns ON said compressor if the pressure detected by said pressure sensor is less than said second reference value.

17. The air feeding device according to claim 12, wherein said pressure controller defines first and second reference values based on said pressure value set by said pressure setting device, said first reference value being greater than said pressure value, said second reference value being less than said pressure value, wherein said pressure controller controls said pressure control valve to open if the pressure detected by said pressure sensor is greater than said first reference value, and wherein said pressure controller controls said pressure control valve to close if the pressure detected by said pressure sensor is less than said second reference value.

18. The air feeding device according to claim 1 in combination with an endoscope, said endoscope including a forceps channel, said outlet of said air feeding device being configured to be coupled to said forceps channel so that the air discharged from said air feeding device flows through said forceps channel through said outlet of said main valve.

19. The air feeding device according to claim 5 in combination with an endoscope, said endoscope including a forceps channel, said outlet of said air feeding device being configured to be coupled to said forceps channel so that the air discharged from said air feeding device flows through said forceps channel through said outlet of said air feeding valve.

20. The air feeding device according to claim 11 in combination with an endoscope, said endoscope including a forceps channel, said outlet of said air feeding device being configured to be coupled to said forceps channel so that the air discharged from said air feeding device flows through said forceps channel through said outlet of said main valve.

21. The air feeding device according to claim 12 in combination with an endoscope, said endoscope including a forceps channel, said outlet of said main valve being configured to be coupled to said forceps channel so that the air discharged from said air feeding device flows through said forceps channel through said outlet of said air feeding valve.

* * * * *